United States Patent [19]

Grasselli et al.

[11] 4,422,980

[45] Dec. 27, 1983

[54] ACRYLIC DIMERIZATION USING SUPPORTED CATALYSTS

[75] Inventors: R. K. Grasselli, Chagrin Falls; J. D. Burrington, Richmond Heights; F. A. Pesa, Aurora; H. F. Hardman, Lyndhurst, all of Ohio

[73] Assignee: Standard Oil Company, Cleveland, Ohio

[21] Appl. No.: 291,708

[22] Filed: Aug. 10, 1981

[51] Int. Cl.$^3$ ............... C07C 121/26; C07C 121/30; C07C 121/00
[52] U.S. Cl. ............................................. 260/465.8 D
[58] Field of Search ................................. 260/465.8 D

[56] References Cited

U.S. PATENT DOCUMENTS

| | | | |
|---|---|---|---|
| 3,449,387 | 6/1969 | Chabardes et al. | 260/465.8 D X |
| 3,450,730 | 6/1969 | Scheben et al. | 260/465.8 D X |
| 3,484,475 | 12/1969 | Cornforth et al. | 260/465.8 D |
| 3,538,133 | 11/1970 | Knoth, Jr. | 260/465.8 D X |
| 3,655,724 | 4/1972 | Linn et al. | 260/465.8 D |
| 3,671,569 | 6/1972 | Chabardes et al. | 260/465.8 D |
| 3,729,498 | 4/1973 | Masada et al. | 260/465.8 D |
| 3,790,617 | 2/1974 | Masada et al. | 260/465.8 D |
| 3,804,868 | 4/1974 | Chabardes et al. | 260/429 J |
| 3,804,869 | 4/1974 | Chabardes et al. | 546/2 X |
| 3,946,066 | 3/1976 | Todd | 260/465.8 D |
| 3,981,900 | 9/1976 | Chabardes et al. | 260/465.8 D |
| 4,089,890 | 5/1978 | Jennings et al. | 260/465.8 D |

OTHER PUBLICATIONS

Strathdee et al., Canadian Journal of Chemistry, 52, (1974), pp. 3000–3007.
McClure et al., J. of Organometallic Chemistry, 12, (1968), pp. P8–P12.
Pittman, Polymer Supported Reactions in Org. Syn. (1980), pp. 249–291, John Wiley & Sons Ltd.
Calmon et al., "Ion Exchangers in Organic and Biochemistry", p. 659, (1957), (Interscience Pub. Inc., N.Y.).

Primary Examiner—Joseph Paul Brust
Attorney, Agent, or Firm—Charles S. Lynch; John E. Miller, Jr.; Larry W. Evans

[57] ABSTRACT

Acrylonitrile is catalytically dimerized using a catalyst comprising a polymer support and a ruthenium complex bonded thereto.

10 Claims, No Drawings

ACRYLIC DIMERIZATION USING SUPPORTED CATALYSTS

BACKGROUND OF THE INVENTION

The present invention relates to the novel technique for dimerizing acrylonitrile to form the corresponding linear dimers, 1,4-dicyanobutane (adiponitrile) and 1,4-dicyanobutenes.

The catalytic dimerization of acrylonitrile is already known. For example, U.S. Pat. No. 3,671,569, the disclosure of which is incorporated herein by reference, teaches that 1,4-dicyanobutenes and adiponitrile can be made by heating acrylonitrile in the liquid phase in the presence of hydrogen and a catalyst comprising a ruthenium compound or complex. U.S. Pat. No. 3,790,617 and U.S. Pat. No. 3,729,498, the disclosures of which are also incorporated herein by reference, further teach that this reaction can be conducted in the vapor phase by employing ruthenium metal or a mixture of a solid ruthenium compound and another compound as the catalyst.

Each of these techniques has its own disadvantages. The liquid phase process is difficult because separation of the expensive liquid phase ruthenium catalyst from the liquid phase products and reactants is difficult. In the vapor phase process, selectivity and single pass yields of the desired linear dimers is low.

Accordingly, it is an object of the present invention to provide a new technique for dimerizing acrylonitrile to the corresponding linear dimers, adiponitrile, cis-1,4-dicyanobutene and trans-1,4-dicyanobutene, which employs a heterogeneous system, i.e. catalyst in a different state than products and reactants, and which provides the desired products with high selectivities and yields.

SUMMARY OF THE INVENTION

This and other objects are accomplished by the present invention in accordance with which acrylonitrile is dimerized in the liquid phase using a solid catalyst comprising a polymeric material having a ruthenium complex bonded thereto.

Thus, the present invention provides a novel process for dimerizing acrylonitrile to product 1,4-dicyanobutenes and/or adiponitrile comprising contacting acrylonitrile with a catalyst at a temperature of 20° to 250° C. in the presence of hydrogen, the catalyst comprising a polymer support having a ruthenium complex bonded thereto, the polymer support comprising an organic polymer backbone having trivalent pendant atoms selected from P, As, Sb, Bi and N covalently bonded thereto and randomly distributed in the polymer, the ruthenium complex being capable of catalyzing the dimerization of acrylonitrile to adiponitrile and/or 1,4-dicyanobutenes and comprising Ru and at least two homogeneous ligands having at least four ligating bonds bonding to the Ru, the Ru in each ruthenium complex datively bonding to a pendant atom in the polymer support, the Ru/pendant atom ratio in the catalyst being at least 0.001, said complex having, on the average, no more than one homogeneous phosphine ligand per atom of ruthenium.

DETAILED DESCRIPTION

Catalyst

The catalyst used in the inventive process is composed of a polymer support having a ruthenium complex bonded thereto via pendant atoms selected from the group consisting P, As, Sb, Bi and N.

The polymer support of the inventive catalyst is composed of an organic polymer backbone carrying the pendant atoms. The nature of the organic polymer backbone is not critical, and any type of polymer can be used. Most conveniently, the polymer backbone is a styrene polymer or copolymer in which the pendant atoms are attached to the phenyl moieties of the polymerized styrene monomers. A particularly good polymer backbone is a styrene divinylbenzene copolymer containing greater than 0 to 50 mole percent, preferably 1 to 30 mole percent, more preferably 2 to 20 mole percent divinylbenzene.

The pendant atoms attached to the polymer backbone serve to strongly bond the ruthenium complex to the polymer backbone. To this end, the pendant atoms must be those which will form strong coordinate bonds with the ruthenium complex. P, As, Sb, Bi and N when in the trivalent state are suitable for this purpose. Phosphorus is the preferred pendant atom. Moreover, mixtures of different pendant atoms can be used on the same polymer backbone.

As appreciated by those skilled in the art, in order that these pendant atoms be trivalent, they must also be bonded to additional groups such as alkyl, aryl, alkoxy, aryloxy, dialkylamido, diarylamido and so forth. The nature of these groups is not critical, but they normally contain no more than twelve carbon atoms.

An important aspect of the catalyst of the invention is that the ruthenium atoms are bonded on the average to no more than two (preferably no more than one) phosphorus atom since higher P/Ru ratios lead to a significant decline in catalytic activity. Accordingly, in the preferred embodiment of the invention when the pendent atom is phosphorus, the amount and distribution of the pendant phosphorus atoms in the polymer are selected so that the ruthenium atoms of the complex will not bond to two or more pendant phosphorus groups. Specifically, the pendant atoms should be randomly distributed in the polymer support and be present in an amount of no more than 15 mole% based on the total number of polymerized monomeric units in the polymer backbone. In the case of a styrene divinyl benzene resin in which the pendant atoms bond to the phenyl moieties of the polymer, this means that the amount of pendant atoms will be no more than about 14 mole% based on the phenyl moieties in the polymer. Usually the amount of pendant atoms will be 0.1 to 14, preferably 0.5 to 7, more preferrably about 5 to 6 mole percent based on the phenyl moieties in the polymer.

Polymers containing less than 15 mole% pendant phosphorus atoms in the trivalent state and randomly distributed throughout the polymer are well known in the art and are commercially available. Any such polymer can be used.

In the preferred embodiment of the invention, the polymer support is composed of the above styrene divinylbenzene copolymer containing 2 to 20 mole% divinylbenzene and in which 0.5 to 7 mole percent, preferably 5 to 6 mole percent of the pendant phenyl groups from the copolymerized styrene contain the phosphine moiety (diphenyl phosphorus) at the para position. This polymer support can be regarded as a terepolymer of 75 to 97.6 mole% styrene, 2 to 20% divinylbenzene and 0.4 to 6% para-diphenylphosphenostyrene.

In accordance with the invention, a ruthenium complex capable of catalyzing the dimerization of acrylonitrile is strongly bonded to the above polymer support via the pendant atom. Such complexes are well known and described, for example, in McClure et al., "Dimerization of Acrylonitrile to 1,4-Dicyano-1-butene with Ruthenium Complexes," *J. Organometal Chem*, Vol. 12, pgs. 8–12, (1968); the Knoth Patent, U.S. Pat. No. 3,538,133; and the previously-mentioned U.S. Pat. No. 3,671,569, U.S. Pat. No. 3,790,617 and U.S. Pat. No. 3,729,498.

In general, suitable ruthenium complexes for use in the present invention are those which (1) will catalyze the dimerization reaction, (2) contain at least two homogeneous ligands having at least four ligating bonds bonding to the ruthenium and (3) have on the average no more than one homogeneous phosphine ligand per atom of ruthenium. "Homogeneous ligands" means ligands not covalently bonded to the polymer backbone.

Examples of such complexes are described by the following general formula

wherein $L^1$ is a mono or bidentate ligand selected from F, Cl, Br, I, acac (2,4-pentanedionate), or mixtures thereof, $L^2$ is one or more of acrylonitrile, methacrylonitrile, acetonitrile, propionitrile, benzonitrile, dimethylsulfoxide, water and a group of the formula

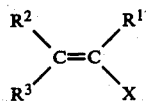

wherein X is CN, $CO_2R^4$, CHO or $CONR_2^4$ and $R^1$, $R^2$, $R^3$ and $R^4$ are independently selected from $C_{1-16}$ alkyl, $C_{1-16}$ aryl and H, and wherein $L^3$ is $R_3^5P$, $R_3^5As$, $R_3^5Sb$, $R_3^6N$ and $R_2^6O$, or mixtures thereof wherein each $R^5$ is a $C_{1-16}$ group independently selected from alkyl, aryl, alkoxy, aryloxy, dialkylamido and diarylamido and $R^6$ is independently selected from $C_{1-16}$ alkyl, $C_{1-16}$ aryl or H, and further wherein a is 1 to 3;
b is 0 to 6;
c is 0 to 6; and
a+b+c is at least 2 and further selected so that $L^1$, $L^2$ and $L^3$ are bonded to the Ru with 4 to 6 ligating bonds, said complex containing on the average no more than one homogeneous phosphine ligand.

Complexes having other mono and bidentate ligands can also be employed.

As indicated above, an important feature of the invention is that the P/Ru ratio in the catalyst of the invention is no more than 2. Preferrably the P/Ru ratio is no more than 1. To this end, the complex should have on the average no more than 1 homogeneous phosphine ligand per ruthenium atom. Preferrably the complex has no homogeneous phosphine ligands.

Preferred ruthenium complexes are those which contain at least two halogen ligands per ruthenium atom and in addition $H_2O$ or acrylonitrile as at least one additional ligand. Particularly preferred ruthenium complexes are $RuCl_3 \cdot 3H_2O$, $Ru(acac)_3$, $RuCl_2(AN)_3$, $RuBr_2(AN)_3$, $RuI_2(AN)_3$.

Other useful complexes are $RuCl_2(AN)_4$, $RuCl_2(CH_3CN)_3$, $RuCl_2$(propionitrile), $RuCl_2(PhCN)_4$, $RuBr_2(AN)_4$, $RuI_2(AN)_4$, $RuCl_2(C_{12}H_{18})$, $RuCl_2(C_4H_8)_3$, $RuCl_2(C_8H_{12})_2$, $RuCl_2(C_8H_{12})$ (p-toluidine), $Ru(stearate)_3$, $Ru(trifluoroacetylacetonate)_3$, $RuCl_3(AsPh_3)_2$, $RuCl_2(SbPh_3)_4$, $[Ru(NH_3)_5Br]Br_2$ and $[Ru(NH_3)_5I]I_2$ wherein AN is acrylonitrile and Ph is phenyl.

The amount of ruthenium complex in the catalyst can vary widely. As a practical matter, the Ru/pendant atom ratio should be at least 0.001 and is preferrably about 0.5 to 1.2. The upper limit is set by the fact that the polymer support will no longer take up complex.

The catalysts of the present invention can be easily prepared by mixing the polymer support and an excess of the ruthenium complex together for a suitable period of time. Preferably, this is accomplished in an inert atomosphere, and, if desired, a suitable solvent for the complex can be included in the system. Compounds which will serve as solvents for the ruthenium complexes are well known in the art. Examples of suitable solvent are methylene chloride, acetone, isopropanol, benzene and toluene.

In a preferred technique of making the catalysts of the invention, the ruthenium complex is added to the polymer support over an extented period of time, either in batches or continuously. It has been found that the ability of the catalyst to produce desired product is significantly enhanced by preparing the catalyst in this way. This discovery is the invention of another and is described in commonly assigned patent application Ser. No. 355,805, filed Mar. 8, 1982.

Specific examples of how to prepare the catalysts of the invention can be found in the following working examples.

Reaction Conditions

The dimerization reaction is carried out in a conventional manner by contacting acrylonitrile with the catalyst for a suitable period of time. Usually, the reaction is carried out at a temperature of 20° to 250° C., preferably 80° to 150° C. for 1 to 100 hours, preferably 1 to 24 hours. The reaction pressure may vary widely with pressures on the order of 1 to 1000 psi, preferably 1 to 500 psi being suitable. Hydrogen must be present in the reaction system. Hydrogen pressures from greater than 0 to 500 psi, are useful with hydrogen pressures of 30 to 200 psi being preferred. The relative amounts of catalyst and acrylonitrile can also vary widely and are normally selected so that the ruthenium/acrylonitrile molar ratio is from $10^{-5}$ to 1, preferably $10^{-3}$ to $10^{-2}$.

It is also preferable in accordance with the present invention to include in the reaction system a small amount of a promoter comprising a weak base having no replaceable hydrogen atoms. Tertiary amines such as N-methylpyrrolidine and triethylamine are effective. Sodium phenoxide, sodium carbonate, sodium cyanide, sodium thiophenol and their potassium and cesium analogs are also effective. Usually the amount of weak base will be such that the base/acrylonitrile motar ratio is zero to 1, preferably about 0.02 to 0.06. By weak base is meant a base with a $pK_b$ of 0 to 8.

As is well known in the art of dimerizing acrylonitrile with ruthenium complexes, certain additional materials will function as cocatalysts promoting the catalytic activity of the ruthenium complexes. These cocatalysts can also be included in the reaction system of the present invention.

WORKING EXAMPLES

EXAMPLE 1

0.4 g of a ruthenium complex comprising $RuCl_2(AN)_3$, 35 ml methylene dichloride and 10 g of a polymer support comprising a random styrene/divinyl benzene para-diphenylphosphenostyrene terepolymer containing 79 mole percent styrene, 20 mole percent divinyl benzene and 1 mole percent para-diphenylphosphenostyrene in the form of beads were stirred together under a nitrogen atmosphere for 24 hours. The beads were then filtered and washed with additional methylene chloride until the solvent was colorless. The beads were then dried under vacuum for 8 hours to produce a catalyst in accordance with the invention having an Ru/P ratio of 0.42.

Into a 300 ml Parr autoclave, 100 mmole acrylonitrile, 0.5 g of the above catalyst, 4 mmole N-methylpyrrolidine, 20 ml acetone solvent and 1 ml $C_{15}H_{32}$ as internal standard for GC analysis were charged. The autoclave was then charged with 80 psi $H_2$ and heated at 110° C. for roughly 4 hours. After the reaction, the reaction mixture was filtered and analyzed by gas chromatography. It was found that 19.8% of the acrylonitrile was reacted with a selectivity to the desired dimer products being 48.0% and a selectivity to by-product propionitrile being 52.0%.

EXAMPLE 2

5 g of the catalyst produced in Example 1, 0.2 g $RuCl_2(AN)_3$ and 35 ml dichloromethane were mixed together under the same procedure described in Example 1 to form a double-impregnated catalyst. The catalyst so obtained had an Ru/P ratio of 0.78. When reacted under the same conditions as in Example 1, it was found that 25.0% of the acrylonitrile charged reacted with a selectivity to the desired dimer products of 57.0% and a selectivity to the by-product propionitrile of 43.0%.

EXAMPLE 3

3 g of the catalyst produced in Example 2 together with 0.2 g $RuCl_2(AN)_3$ and 30 ml methylene dichloride were charged into a Schlenk flask and the mixture stirred under nitrogen for 24 hours. The polymer beads were filtered, washed with methylene dichloride until the was liquid was colorless and dried under vacuum for 8 hours. A catalyst in which the Ru/P ratio was 0.80 was produced.

The catalyst obtained was used for the dimerization of acrylonitrile under the same reaction conditions as in Examples 1 and 2. Acrylonitrile conversion was found to be 23.0% with a selectivity to the desired dimer products of 62.0% and a selectivity to propionitrile by-product of 38.0%.

EXAMPLE 4

1.0 of the same polymer beads used in Example 1 was placed in a 50 ml round bottomed flash and 5 ml methylene dichloride added. 0.1 g $RuCl_2(AN)_3$ was dissolved in 20 ml methylene dichloride and the mixture placed in a 20 ml gas tight syringe pump. The flash was capped with a rubber septum and kept under a nitrogen atmosphere while the solution in the flash was continuously stirred for a period of 24 hours. For the first 20 hours, the $RuCl_2(AN)_3$ solution was charged into the flask by the syringe pump at a rate of 1 ml per hour. After 24 hours, the beads were filtered, washed with methylene chloride until the wash liquid was colorless and dried under vacuum for 8 hours. Thd catalyst obtained was found to have an Ru/P ratio of 1.07.

The catalyst obtained was tested in the dimerization of acrylonitrile in the same way as Examples 1 to 3. The acrylonitrile conversion was 12.0% while the selectivity to the desired dimer products was 57.0% and the selectivity to propionitrile by-product was 43.0%.

EXAMPLES 5 to 15

Examples 1 to 4 were repeated using various different ruthenium complexes, polymer supports and preparational techniques. In each example, the polymer support was composed of a terepolymer of styrene, divinylbenzene and para-diphenylphosphenostyrene, the polymers containing 2 to 20% divinylbenzene and 1 to 10% para-diphenylphospenostyrene. The nature of the catalyst as well as the result obtained are set forth in the following table.

TABLE 1

| Example No. | Polymer Support % DVB | Polymer Support % PPh2 | Ru Complex | Number of Impregnations | Solvent | Ru/P in Catalyst | CONVERSION % | SELECTIVITY Propionitrile | SELECTIVITY Dimer |
|---|---|---|---|---|---|---|---|---|---|
| 1 | 20 | 1 | $RuCl_2(AN)_3$ | 1 | $CH_2Cl_2$ | 0.42 | 19.8 | 52.0 | 48.0 |
| 2 | 20 | 1 | $RuCl_2(AN)_3$ | 2 | $CH_2Cl_2$ | 0.78 | 25.0 | 43.0 | 57.0 |
| 3 | 20 | 1 | $RuCl_2(AN)_3$ | 3 | $CH_2Cl_2$ | 0.80 | 23.0 | 38.0 | 62.0 |
| 4 | 20 | 1 | $RuCl_2(AN)_3$ | continuous | $CH_2Cl_2$ | 1.07 | 12.0 | 43.0 | 57.0 |
| 5 | 20 | 4–6 | $RuCl_3.3H_2O$ | 2 | $CH_3OH$ | 0.11 | 38.0 | 71.0 | 29.0 |
| 6 | 20 | 4–6 | $RuCl_2(AN)_3$ | 2 | $CH_3OH$ | 0.64 | 30.0 | 48.0 | 52.0 |
| 7 | 20 | 4–6 | $RuCl_2(AN)_3$ | 2 | $CH_2Cl_2$ | 0.45 | 38.0 | 32.0 | 68.0 |
| 8 | 20 | 4–6 | $RuCl_2(AN)_3$ | 1 | $CH_2Cl_2$ | 0.26 | 48.0 | 59.0 | 41.0 |
| 9 | 20 | 4–6 | $RuCl_2(AN)_3$ | 1 | $CH_2Cl_2$ | 0.22 | 57.0 | 55.0 | 45.0 |
| 10 | 2 | 4–6 | $RuCl_2(AN)_3$ | 1 | $CH_2Cl_2$ | 1.20 | 46.0 | 41.0 | 59.0 |
| 11 | 5 | 10 | $RuCl_2(AN)_3$ | 1 | $CH_2Cl_2$ | 0.26 | 18.0 | 57.0 | 43.0 |
| 12 | 20 | 6 | $RuCl_2(AN)_3$ | 1 | $CH_2Cl_2$ | 0.10 | 12.6 | 46.0 | 54.0 |
| 13 | 20 | 1 | $RuCl_3.3H_2O$ | 1 | Acetone | 0.99 | 18.0 | 41.0 | 59.0 |
| 14 | 20 | 4–6 | $RuCl_2(AN)_3$ | continuous | $CH_2Cl_2$ | 0.26 | 25.0 | 49.0 | 51.0 |
| 15 | 2 | 4–6 | $RuCl_2(AN)_3$ | continuous | $CH_2Cl_2$ | 0.47 | 48.0 | 56.0 | 44.0 |

Table 1 shows that acrylonitrile can be dimerized to the desired linear dimer products, adiponitrile and 1,4-dicyanobutenes, with good acrylonitrile conversions and good selectivities to the desired dimer products. In addition, from Examples 1 to 4 it can be seen that the catalytic properties of the catalysts of the invention are improved if the ruthenium complex is added over an extented period of time during catalyst preparation rather than all at once.

EXAMPLE 16

A catalyst in accordance with the present invention in which the polymer support is a para-diphenylphosphenostyrene terepolymer containing 75 mole percent styrene, 20 mole percent divinyl benzene and 5 mole percent para-diphenylphosphenostyrene in the form of beads and the ruthenium complex is $RuCl_2(AN)_3$, the catalyst having an Ru/P ratio of 1.7 is used repeatedly to dimerize acrylonitrile in accordance with the invention. In each cycle of operation, the reaction system included pyrrolidine as promoter and acetone as a solvent, with the acrylonitrile/Ru ratio being 500, the reaction time being 5 hours, the pyrrolidine/acrylonitrile motar ratio being 0.04, the hydrogen pressure being 80 psig and the reaction temperature being 110° C. After each cycle of operation, the catalyst was removed from the reaction system by filtration and used as the catalyst in the subsequent cycle of operation. The results obtained are set forth in the following Table 2.

TABLE 2

CONDITIONS: Ru/P = 1.7, 110° C., 80 psig $H_2$, AN/Ru = 500, 5 hr. rx time, pyrrolidine/AN = 0.04, solvent = acetone

| CYCLE | AN CONVERSION | SELECTIVITY DIMER | PROPIONITRILE |
|---|---|---|---|
| 1 | 35 | 50 | 47 |
| 2 | 18 | 64 | 36 |
| 3 | 23 | 53 | 47 |
| 4 | 11 | 52 | 48 |

The above Table 2 shows that the catalysts of the invention can be easily separated from the reaction medium and reused repeatedly without significant loss in activity. In other words, the above data illustrates that the catalytic ruthenium complex remains bound on the polymer support even after reaction and is not lost to the system through dissolving in the liquid reaction medium.

Although only a few embodiments of the invention have been described above, it should be appreciated that many modifications can be made without departing from the spirit and scope of the invention. All such modifications are intended to be included within the scope of the invention, which is to be limited only by the following claims:

We claim:

1. A process for dimerizing acrylonitrile to produce adiponitrile and/or 1,4-dicyanobutenes comprising contacting acrylonitrile with a catalyst at a temperature of 20° to 250° C. in the presence of hydrogen, said catalyst comprising a polymer support having a ruthenium complex bonded thereto, said polymer support comprising an organic polymer backbone having trivalent P pendant atoms covalently bonded thereto and randomly distributed in said polymer, said ruthenium complex being capable of catalyzing the dimerization of acrylonitrile to adiponitrile and/or 1,4-dicyanobutenes and comprising Ru and at least two homogeneous ligands having at least four ligating bonds bonding to said Ru, the Ru in each ruthenium complex datively bonding to a pendant atom in said polymer support, the Ru/pendant atom ratio in said catalyst being at least 0.001, said complex being substantially free of homogeneous phosphine ligands.

2. The process of claim 1 wherein said polymer backbone is a styrene polymer or copolymer.

3. The process of claim 2 wherein said polymer is a polymer of styrene and divinylbenzene.

4. The process of claim 3 wherein said polymer support is a terepolymer of 2 to 20% divinylbenzene, 0.4 to 6% para-diphenylphosphenostyrene and the balance styrene.

5. The process of claim 4 wherein said ruthenium complex is defined by the formula $$RuL_a^1 L_b^2 L_c^3$$

wherein $L^1$ is a mono or bidentate ligand selected from F, Cl, Br, I, acac, or mixtures thereof, $L^2$ is one or more of acrylonitrile, methacrylonitrile, acetonitrile, propionitrile, benzonitrile, water and a group of the formula

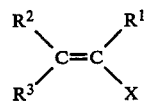

wherein X is CN, $CO_2R^4$, CHO or $CONR_2^4$ and $R^1$, $R^2$, $R^3$ and $R^4$ are independently selected from $C_{1-16}$ alkyl, $C_{1-16}$ aryl and H, and wherein $L^3$ is $R_3^5P$, $R_3^5As$, $R_3^5Sb$, $R_3^6N$ and $R_2^6O$, or mixtures thereof wherein each $R^5$ is a $C_{1-16}$ group independently selected from alkyl, aryl, alkoxy, aryloxy, dialkylamido and diarylamido and $R^6$ is independently selected from $C_{1-16}$ alkyl, $C_{1-16}$ aryl or H, and further wherein a is 1 to 3;

b is 0 to 6;

c is 0 to 6; and a+b+c is at least 2 and further selected so that $L^1$, $L^2$ and $L^3$ are bonded to the Ru with 4 to 6 ligating bonds.

6. The process of claim 5 wherein at least two ligands in said ruthenium complex are halogen atoms and further wherein at least one additional ligand in said ruthenium complex is $H_2O$ or acrylonitrile.

7. The process of claim 4 wherein said ruthenium complex is $RuCl_2(AN)_3$.

8. The process of claim 3 wherein said ruthenium complex is defined by the formula $$RuL_a^1 L_b^2 L_c^3$$

wherein $L^1$ is a mono or bidentate ligand selected from F, Cl, Br, I, acac, or mixtures thereof, $L^2$ is one or more of acrylonitrile, methacrylonitrile, acetonitrile, propionitrile, benzonitrile, dimethylsulfoxide, water and a group of the formula

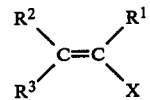

wherein X is CN, $CO_2R^4$, CHO or $CONR_2^4$ and $R^1$, $R^2$, $R^3$ and $R^4$ are independently selected from $C_{1-16}$ alkyl, $C_{1-16}$ aryl and H, and wherein $L^3$ is $R_3^5P$, $R_3^5As$, $R_3^5Sb$, $R_3^6N$ and $R_2^6O$, or mixtures thereof wherein each $R^5$ is a $C_{1-16}$ group independently selected from alkyl, aryl, alkoxy, aryloxy, dialkylamido and diarylamido and $R^6$ is independently selected from $C_{1-16}$ alkyl, $C_{1-16}$ aryl or H, and further wherein a is 1 to 3;
b is 0 to 6;
c is 0 to 6; and
a+b+c is at least 2 and further selected so that $L^1$, $L^2$ and $L^3$ are bonded to the Ru with 4 to 6 ligating bonds.

9. The process of claim 1 wherein said ruthenium complex is defined by the formula $$RuL^1_a L^2_b L^3_c$$

wherein $L^1$ is a mono or bidentate ligand selected from F, Cl, Br, I, acac, or mixtures thereof, $L^2$ is one or more of acrylonitrile, methacrylonitrile, acetonitrile, propionitrile, benzonitrile, dimethylsulfoxide, water and a group of the formula

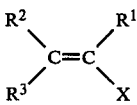

wherein X is CN, $CO_2R^4$, CHO or $CONR^4_2$ and $R^1$, $R^2$, $R^3$ and $R^4$ are independently selected from $C_{1-16}$ alkyl, $C_{1-16}$ aryl and H, and wherein $L^3$ is $R^5_3P$, $R^5_3As$, $R^5_3Sb$, $R^6_3N$ and $R^6_2O$, or mixtures thereof wherein each $R^5$ is a $C_{1-16}$ group independently selected from alkyl, aryl, alkoxy, aryloxy, dialkylamido and diarylamido and $R^6$ is independently selected from $C_{1-16}$ alkyl, $C_{1-16}$ aryl or H, and further wherein a is 1 to 3;
b is 0 to 6;
c is 0 to 6; and
a+b+c is at least 2 and further selected so that $L^1$, $L^2$ and $L^3$ are bonded to the Ru with 4 to 6 ligating bonds.

10. The process of claim 5 wherein the ruthenium/acrylonitrile ratio is $10^{-3}$ to $10^{-2}$.

* * * * *